United States Patent
Wyatt

(10) Patent No.: US 8,163,182 B2
(45) Date of Patent: Apr. 24, 2012

(54) COMPARTMENTALIZED FIELD FLOW FRACTIONATION

(75) Inventor: Philip J. Wyatt, Santa Barbara, CA (US)

(73) Assignee: Wyatt Technology Corporation, Santa Barbara, CA (US)

(*) Notice: Subject to any disclaimer, the term of this patent is extended or adjusted under 35 U.S.C. 154(b) by 0 days.

(21) Appl. No.: 12/790,707

(22) Filed: May 28, 2010

(65) Prior Publication Data

US 2011/0290724 A1    Dec. 1, 2011

(51) Int. Cl.
*B01D 63/00*    (2006.01)
*B01D 11/00*    (2006.01)

(52) U.S. Cl. ... 210/637; 210/634; 210/808; 210/321.65; 210/321.75

(58) Field of Classification Search .......... None
See application file for complete search history.

(56) References Cited

U.S. PATENT DOCUMENTS

| | | | |
|---|---|---|---|
| 4,440,638 A | 4/1984 | Judy et al. | |
| 5,141,651 A * | 8/1992 | Giddings | 209/18 |
| 5,193,688 A * | 3/1993 | Giddings | 209/155 |
| 6,905,029 B2 * | 6/2005 | Flagan | 209/210 |

FOREIGN PATENT DOCUMENTS

| | | |
|---|---|---|
| WO | WO 00/47322 A2 | 8/2000 |
| WO | WO 01/96025 A2 | 12/2001 |
| WO | WO 2006/063625 A1 | 6/2006 |

OTHER PUBLICATIONS

Schimpf et al., "Channel Components", Field-Flow Fractionation Handbook, 2000, p. 279-295999.*
Podzimek et al., Asymmetric Flow Field Flow Fractionation: A Powerful Method for Polymer Characterization, 2009.*
J. C. Giddings, Field Flow Fractionation: Analysis of Macromolecular, Colloidal, and Particulate Materials, Science, 1993, pp. 1456-1465, V 260, AAAS, USA.
K.-G. Wahlund and J.C. Giddings, Properties of an Asymmetrical Flow Field-Flow Fractionation Channel Having One Permeable Wall, Anal. Chem., 1987, pp. 1332-1339, V 59, ACS, USA.
Wyatt Technology Corporation, Eclipse 3+ promotional literature, 2009, Wyatt Technology Corporation, Goleta, USA.
FFFractionation, Ltd., Instrument Manual for Model F-1000 Universal Fractionator, Instrument manual, 1994, FFFractionation, Ltd., Salt Lake City, USA.
M. E. Schimpf, K. C. Caldwell, J.C. Giddings (Eds.), Field Flow Fractionation Handbook, 2000, Wiley-Interscience, USA.

* cited by examiner

*Primary Examiner* — Vickie Kim
*Assistant Examiner* — Allison M Gionta
(74) *Attorney, Agent, or Firm* — Philip J. Wyatt; David N. Villalpando

(57) ABSTRACT

A field flow fractionator to separate particles contained within an injected sample aliquot is described. As required, said fractionator may be used to capture, for subsequent removal, specific predefined classes of such particles. Based upon the cross flow or asymmetric flow field flow fractionators, the fractionator disclosed contains means to vary the applied transverse flows at a plurality of locations along the length of its separating channel. A plurality of separated compartments, each lying below a distinct and corresponding membrane supporting permeable frit segment, are provided individual means to control the localized flow through the membrane section thereabove. A corresponding concentric compartment implementation achieves the same type of compartmentalized cross flow when integrated with a hollow fiber fractionator.

4 Claims, 10 Drawing Sheets

DETAIL A

COMPARTMENTALIZED FIELD FLOW FRACTIONATION

RELATED APPLICATIONS AND PATENTS

The following patents and applications relate to similar characterizations of separated molecules and small particles:

U.S. Pat. No. 6,774,994, P. J. Wyatt and M. Weida "Method and apparatus for determining absolute number densities of particles in suspension" 10 Aug. 2004.

P. J. Wyatt, M. H. Chen, and D. N. Villalpando "Method and apparatus for optimizing the separation of small particles using Asymmetric Flow Field Flow Fractionation," Ser. No. 12/157,367, filed 9 Jun. 2008.

BACKGROUND

Throughout this specification, the term "particle" refers to the constituents of liquid sample aliquots that may be molecules of varying types and sizes, nanoparticles, virus like particles, liposomes, emulsions, bacteria, colloids, etc. Their size range may lie between 1 nm and several thousand micrometers.

The separation of particles in a solution by means of field flow fractionation, FFF, was studied and developed extensively by J. C. Giddings beginning in the early 1960s. The basis of these techniques lies in the interaction of a channel-constrained sample and an impressed field applied perpendicular to the direction of flow. Among those techniques of current interest is cross flow FFF, often called symmetric flow or SF1FFF, whereby an impressed field is achieved by introducing a secondary flow perpendicular to the sample borne fluid within the channel. There are several variations of this technique including asymmetric flow FFF, or A4F, and hollow fiber, or H4F, flow separation.

Other FFF techniques include sedimentation FFF, SdFFF, wherein a gravitational/centrifugal cross force is applied perpendicular to the direction of the channel flow; electrical FFF, EFFF, wherein an electric field is applied perpendicular to the channel flow; and thermal FFF, ThFFF, wherein a temperature gradient is transversely applied. As the application of a particular FFF technique is achieved by means of a corresponding device, said application will be referred to herein as a type of "field flow fractionator."

Common to all these field flow fractionators is a fluid, or mobile phase, into which is injected an aliquot of a sample whose separation into its constituent fractions is achieved by the application of the cross field. Many of the field flow fractionators allow for the control and variation, during the time the sample aliquot flows down the channel, of the channel flow velocity and the strength of the applied cross field. Common also to these field flow fractionators is the fact that only the cross field and channel flow rates may be varied and, only then, throughout the entire region in which the separation is occurring. Although such programming is capable of producing effective separations for a wide variety of particle classes, it has associated limitations.

An illustration of such limitations relates to the separation of particles by means of a symmetric flow cross flow fractionator. As the sample aliquot begins to undergo non-steric separation while it moves down the channel, the smaller particles lead the larger ones. By increasing the cross flow rate, the separation of all species continues yet the larger fractions begin to trail further behind their smaller sized companions. With sufficient cross flow, these larger fractions may be slowed down considerably while the smaller particles have already completed their traversal of the channel producing their associated fractionation. By this time, the smaller fractions, though separated, may have been diluted significantly so that their local peaks have broadened and their associated concentration diminished. Upon leaving the channel, subsequent analyses using various detection means may be unable to detect fractions of such correspondingly very low concentration. While the retained larger particles as yet may not have had sufficient time to complete their passage through the channel and to separate therein, the smaller particles may have long left the channel and no longer, therefore, be subject to the cross forces needed to continue their separation. Indeed, the separation of substantially larger particles, say, within the range of 500 to 1000 nm requires considerably different channel and cross flow rates than might be required to separate particles within the range of 5 to 10 nm. The separation of samples whose sizes extend over very large size ranges requires considerable flexibility in programming the relative channel and cross flow rates during the passage of such sample aliquots through the channel selected. Optimal fractionation of one group of sizes does not insure an equivalent or even comparable fractionation of another group of sizes.

A continuing problem for such FFF separations lies in the historic inability of these techniques to vary local flow conditions within the channel. Heretofore, control of the fractionation process, irrespective of the FFF method, has been directed to the entire channel. It is the major objective of the inventive methods and field flow fractionators described herein to permit localized control over the applied flow and forces. By these means, the flows and forces may be controlled at specific local regions throughout the length of the fractionating channel.

Although most of the illustrations of the new fractionation method presented will be in the context of cross flow based separations, as will be obvious to those skilled in the art, the methods disclosed will be applicable equally to other field flow fractionators. The most important class of such field flow fractionators, in terms of the sheer numbers of scientific papers referring thereto, is that referred to as asymmetric flow field flow fractionation, or A4F, and invented by Karl-Gustav Wahlund. A brief review of the technique is provided later.

The A4F fractionator is considered a variation of the earlier developed symmetrical flow field fractionator, SF1FFF. In this earlier device, a cross flow is provided to the channel by a separate pump. Thus each flow is produced by a separate pump providing, thereby, crossflow symmetry. For A4F, on the other hand, an effective cross-flow is established by restricting the channel out flow relative to the input flow. The difference between the two flows becomes the effective cross flow. Because the A4F fractionator produces the two basic flow fields of the traditional SF1FFF device with a single pump, many of the results characteristic of symmetrical cross-flow FFF have been assumed operative for A4F, as well. One of these, for example, is the so-called fractionating power F that is proportional to the product of cross flow $f_x$ times the square root of the ratio of cross flow to channel-flow, $f_c$, i.e.

$$F \propto f_x \times \sqrt{\frac{f_x}{f_c}}.$$

Since the source of the cross-flow for the symmetrical fractionator is independent of the channel flow, both may be varied and would be constant over the channel length. For the A4F device, on the other hand, the channel flow always varies along the length of the channel and reaches a minimum just before the sample leaves the channel.

In order to compensate for this decrease in channel flow and to provide an associated constancy of the cross-flow per unit area, a variety of techniques have been employed. These include programming the cross-flow by varying the mobile phase input flow rate and changing the impedance to the cross flow. A variety of channel shapes have been tried including trapezoidal and exponential with the hope of preserving a greater channel flow near the outlet. The tapered channel, decreasing its width along its length, allows the channel flow per unit area to be increased sufficiently to compensate for its diminution necessary to provide the corresponding cross flow.

There are other difficulties with the A4F fractionator despite its superficial simplicity. First, there is a common problem to both SF1FFF and A4F: the four surfaces that define the channel are of different materials and one of them may depart from the expected laminar flow patterns of the theory. Indeed, the frit-supported membrane, of the accumulation wall, is soft and porous which is quite distinct from the exemplar sedimentation field flow fractionator, or SdFFF, wherein all walls, generally the sides of stainless steel tubing, are smooth and of the same materials. Laminar flow confined by such surfaces does produce the expected parabolic flow profile with the tangential flow reaching zero at the walls. For both A4F and SF1FFF flow, however, conditions at the membrane boundary are not well understood.

It is a major objective of this invention to establish, by reference to the A4F fractionator and its associated methods of application, a new type of separation capability having greater versatility by means of a different type of frit support structure and an associated set of cross flow regulators. This inventive frit structure will permit the cross flow per unit membrane area to be variable at different regions of the channel. Because if this variability, another objective of the invention is achieved: the selective filtering of larger particle components of a sample undergoing fractionation. Another objective of the invention is to sharpen broadened species peaks that had been resolved/separated earlier within the channel.

All of the objectives of this new inventive A4F-based fractionator are applicable to most classes of FFF techniques that might be modified to allow for external control of the cross field at discrete regions along the associated channel. These include the symmetrical cross flow fractionator, hollow-fiber fractionator, and, to some extent, the electrical field flow fractionator.

A further objective of the inventive method is its enhanced ability to capture and identify outlier particle populations. This, in turn, may be used in appropriate circumstances to purify certain classes of solutions that may be contaminated by such undesirable and potentially dangerous particulates, returning them, thereby, to a requisite pristine condition.

SUMMARY OF THE INVENTION

A new type of field flow fractionation building on the basic structure of the SF1FFF and A4F concepts is described wherein the membrane supporting frit is comprised of distinct regions/compartments, transverse to the direction of channel flow, with correspondingly distinct cross flows programmable therethrough. This segmented structure permits a new class of separation based fractionations to be achieved. For example, following fractionation of a sample by a traditional A4F device, the peaks associated with fractions separated thereby, though resolved, remain diluted and broadened relative to the peak width of the unfractionated injected sample aliquot. With the inventive device, the separated peaks may be re-concentrated and sharpened at different regions along the channel.

The new device, hereinafter referred to as compartmentalized field flow fractionation, or CFFF, may be applied also to capture and/or retain outliers. Once captured, such particles may be retained for later analyses or removed from the solution entirely. This latter application may be used to restore pharmaceuticals contaminated with potentially immunogenic particulates to their previous pristine state. For this application, an early region of the channel is programmed to provide sufficient cross flow to retain or delay significantly particles above a specified size threshold, while fractions comprised of smaller particles proceed through A4F device more rapidly. Following the emergence of the smaller particles at the channel exit port, the delayed particles are released for capture or removal upon their emergence from the channel.

The ability to regulate cross flows at different regions of the channel permits selective particle movement restriction to be applied successively during a sample's transport through the channel. Thus, accompanying smaller fractions may be selectively accelerated relative to larger sample constituents and, thereby, separated therefrom. Once so-separated, such samples may be reconcentrated by restricting their local channel movement once they arrive at a later region.

The multi-region frit structure, each region of which provides a selectable cross flow into a specific compartment therebelow, is capable of a wide variety of separations heretofore not possible within the traditional A4F and SF1FFF structures. Indeed, the capabilities of CFFF are so broad and extensive that the apparatus and means for their control open up new vistas for the study and application of the FFF process itself. Such a generalized frit structure allows simultaneous separations of complex particle distributions that may be present within a single injected sample.

Corresponding to the segmented frit regions, the supported membrane itself may be segmented to provide a selected permeability for the sample fractionation passing over it, at which moment the fraction may be diverted directly therethrough.

Means by which the method may be applied as well to other types of FFF such as hollow fiber FFF, and electrical FFF are mentioned.

DETAILED DESCRIPTION OF THE INVENTION

Figure 1:
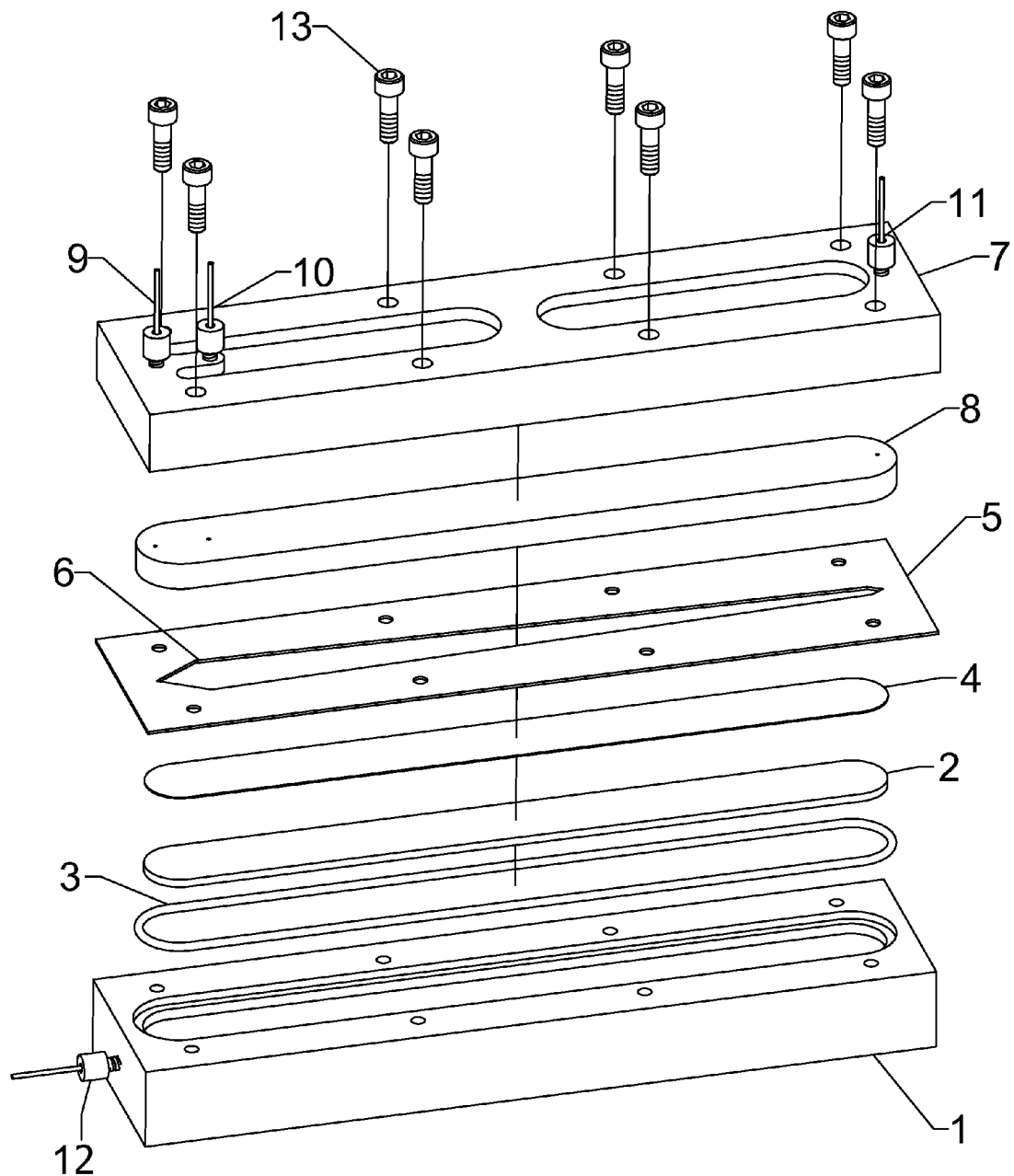
FIG. 1 shows the structure and key elements of a standard A4F channel.

We begin with a review of the elements of an asymmetric flow FFF channel. The A4F channel, illustrated in FIG. 1, is comprised of the following elements together with means to hold them together:
1) a bottom assembly structure 1 holding a liquid-permeable frit 2 surrounded by a sealing O-ring 3,
2) a permeable membrane 4 that lies on the frit 2,
3) a spacer 5 of thickness from about 75 μm to 800 μm into which has been cut a cavity 6, and
4) a top assembly structure 7 generally holding a transparent plate 8 of material such as Lexan® or glass. The plate need not be transparent for some implementations.

The resulting sandwich is held together with bolts 13 or other means. The generally coffin-shaped or tapered cavity 6 in the spacer 5 will serve as the channel in which separation will occur. The top assembly structure 7 usually contains three holes, called ports, that pass through the top plate 8 and are centered above the channel permitting the attachment of fittings thereto. These ports are:
1) a mobile phase inlet port 9 located near the beginning of the channel and through which is pumped the carrier liquid, the so-called mobile phase,
2) a sample port 10, downstream of the inlet port, into which an aliquot of the sample to be separated is introduced to the channel and focused thereunder, and
3) an exit port 11 through which the fractionated aliquot leaves the channel near the end of the cavity.

A single pump, as used in the A4F preferred embodiment, provides the mobile phase at the inlet port 9. The mobile phase is the source of two distinct flows: i) flow through the frit-supported membrane producing a cross flow transverse to the injected sample, and ii) longitudinal flow parallel to the membrane and leaving the channel with the fractionated sample through the exit port 11. Because of the small diameter of the outlet tubing as well as back pressure caused by detectors downstream of the channel, the impedance to the sample-containing channel flow is generally much greater than the impedance produced by the frit-supported membrane and the cross flow therethrough. This cross flow is controlled by a needle valve or similar computer interfaced means housed in a remote control unit. The total flow that passes through the membrane 4 and, therefrom, through the supporting frit 2, is controlled and regulated by means of a remote valve that controls the outflow through port fitting 12. Similar A4F devices to those manufactured by Wyatt Technology Corporation, and as discussed explicitly in this specification, are manufactured by ConSenxus GmbH and PostNova Analytics Inc. Both of these achieve the same type of separation.

Thus if the mobile phase inlet flow at 9 is, say, 2 ml per minute and the flow through the outflow controlling needle valve programmed to provide 0.5 ml/min through 12, the total outlet flow through 11 would be 1.5 ml/min. Thus the single needle valve controller regulates the split of the mobile phase into two components: the total so-called cross flow through the membrane 4 and exiting through 12 and, the remaining outflow through 11. Recall that the outflow through 11 is subject to a large impedance/back pressure arising from its narrow outlet and the detectors downstream. The supporting frit is very porous and produces negligible impedance to flow through it.

Prior to separation, a sample aliquot is injected at the sample injection port 10 and a reversed flow, created by a partial split off from the normal mobile phase stream, is introduced through the exit port 11. The two counter flows keep the injected sample aliquot in position under its injection port 10, focusing it thereby within a small region transverse to the usual longitudinal channel flow. This "stop-flow" mode allows the aliquot to equilibrate. Once equilibrated, the sample aliquot is released by restoring the channel flow. The thus-focused aliquot will fractionate as it is driven forward by the channel flow while a transverse component acts to drive it downward toward the frit-supported membrane, or the often used term "accumulation wall."

Instead of applying the stop flow technique with focusing to allow the sample aliquots to equilibrate, the conventional procedure for A4F, the earlier developed symmetric cross flow FFF, SF1FFF, provided for the sample to be injected directly into the mobile phase and retained at the inlet frit for a sufficient time to permit relaxation before release to the symmetric flow separation channel.

Once the particles have been separated by the A4F unit, they are generally examined by means of different classes of detection instruments responsive thereto. These may include light-scattering photometers, UV absorption meters, differential refractive index detectors, differential viscometers, and combinations thereof. Such devices are used to characterize the separated particles/molecules in terms of their molar mass, intrinsic viscometry, size, etc.

Figure 2:
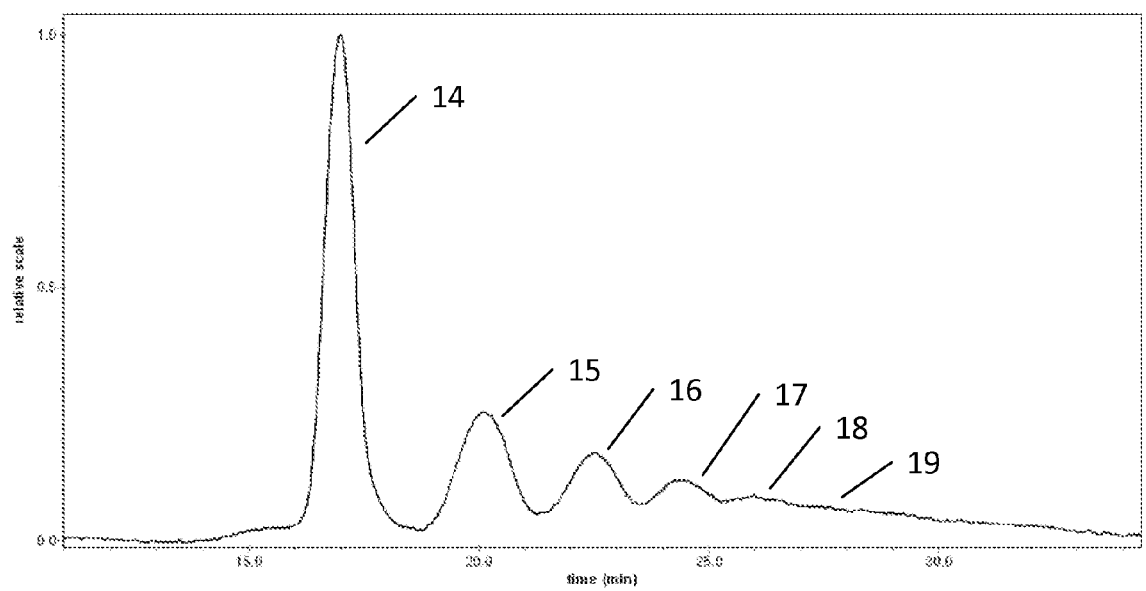
FIG. 2 shows the results of a conventional separation of a degraded BSA sample as detected by a multiangle light scattering photometer at 90° subsequent to the A4F fractionation.

FIG. 2 shows the 90° light scattering signal as a function of time from a bovine serum albumin, BSA, sample fractionated by an A4F device. Note that the sample is comprised of 5 peaks, 14, 15, 16, 17 and 18 in addition to other unresolved elements 19. The resolved peaks include certain so-called oligomers that are small 2-, 3-, 4-, and 5-mer aggregates of the monomer, respectively. The major peak at 14 corresponds to the monomer fraction. Pharmaceutical products, somewhat similar to this protein example, must be produced in such a manner that the amount of aggregated monomer is negligible. Although such oligomers do not contribute generally to the biological's therapeutic activity, their presence should be minimized. Of even greater importance are much larger aggregates that may cause immunogenic responses in the patient. In this manner, the biological becomes dangerous to the patient and must be cleared of such possible contributions. An objective of this invention is to show how this might be achieved.

Note the width of the eluting peaks of FIG. 2. For example, note that the monomer peak 14 elutes over the range from about 16 min to 18.7 min, i.e. a total width of about 2.7 min. If the peak could now be narrowed to, say, a range corresponding to about 1.0 min without affecting the separation of this peak relative to adjacent oligomers peaks 15, 16, 17 and 18 in the process, the concentration within the reduced 0.5 ml band would have been increased approximately by the ratio 2.7/1.0=2.7. It is an important objective of the present invention to achieve such increased concentrations when desirable. We shall refer to this process of increasing the peak concentrations by such narrowing as "reconcentrating."

Perhaps of even greater importance would be the separation of the larger aggregate elements beyond the last oligomeric state observed. Indeed, the contributions that elute beyond 28 min should be examined in greater detail for their possible inclusion of larger aggregates that may be immunogenic. Another objective of this invention is to separate and concentrate such contributions for later collection and analyses. In addition, if such immunogenic contributions are known to be present, the product cannot be sold and is generally destroyed. On the other hand, if these contaminants could be removed, the product might then be considered safe and could be marketed as such. An additional objective of this invention is to be able to restore such contaminated pharmaceutical products to pristine, safe, and marketable states.

Figure 3:
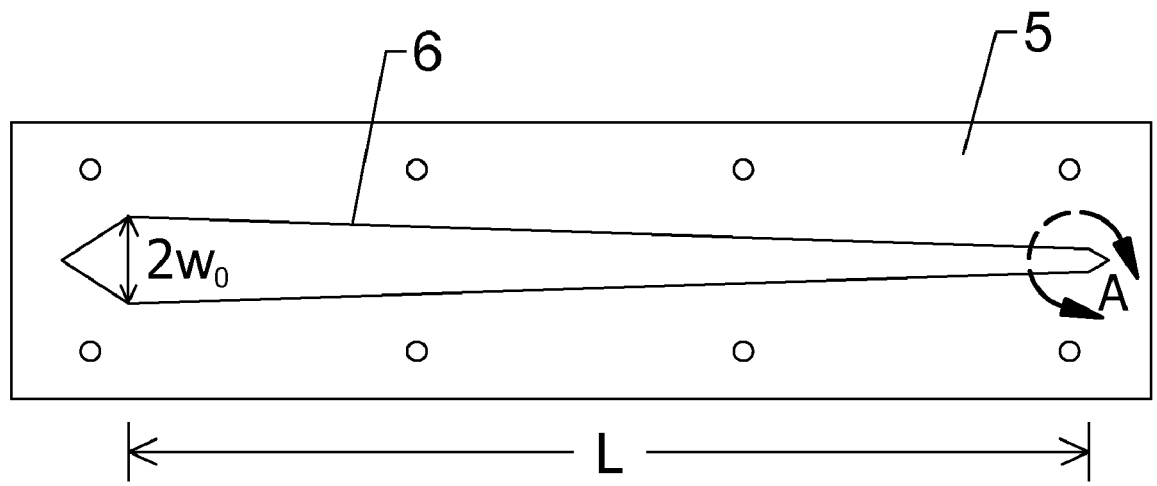
FIG. 3 shows a tapered channel structure employed to maintain constant channel flow per unit channel area.
Figure 3:
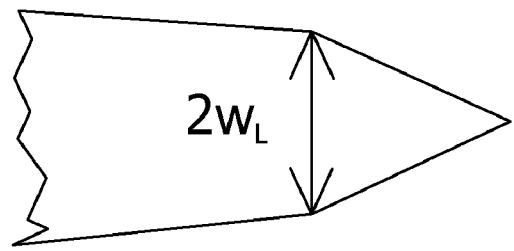

The channel flow of a conventional A4F unit decreases along the length of the channel. This is quite distinct from the SF1FFF system wherein separate pumps provide constant cross and channel flows. Thus for the A4F systems, the fractionating power may increase slightly down the length of the channel. However, in order to keep the ratio of channel flow to cross flow per unit area constant, the channel is usually tapered. FIG. 3 illustrates such a channel 6 cut into a spacer 5 of length L, initial width $2w_0$, and final width $2w_L$. At any position x, the width of the channel is given by $w(x)=2w_0 (1 - bx)$, where $$b = \frac{w_0 - w_L}{Lw_0}.$$

Thus, the channel flow rate at any position along such a tapered channel is $f = f_0 \, F \int_0^x w(x)dx$, where $$F = \frac{c_{cr}}{A},$$

$c_{cr}$, is the total cross flow through the channel-defined membrane, $f_0$ is the input flow rate, and A is the area of the channel from 0 to L. By tapering the channel, the channel flow f in excess of the component that is locally diverted to cross flow is increased approximately in its rate per unit area in the ratio of $w_0/w(x)$, where the channel width at a distance x is $2w(x)$ Since the channel flow to cross flow ratio for the A4F device varies throughout the length of the channel, any attempt to change this ratio at one region of the channel necessarily affects this ratio throughout the channel. Indeed, characteristic of A4F operation has been the programming of these flows during the separation and elution of the sample. Until the current invention, the possibility of more localized control had been neither possible nor considered. Consider now the preferred implementation of the invention shown in FIG. 4 wherein the frit is divided into N separate regions 20, $R_i$, i=1, ..., N. For example, the first three compartments (and their corresponding frit regions) shown in FIG. 4 might be replaced by a single larger compartment (and a correspondingly larger frit region). The successive compartments and frit regions may be combined as well. Below each region 20 is a corresponding partitioned compartment 21 through whose base is an exit port fitting 12. Flow through each such exit port fitting 12 is controlled by a corresponding programmable needle valve means $V_i$, i=1, ..., N, that regulates the flow through its supporting frit region. A plurality of programmable regulators, one for each compartment/region, are located in an external control unit. Needle valves combined with flow meter regulation are often selected for this purpose. As the cross flow through each region may be individually programmed in time, the inventive system provides a broad range of capabilities. Larger particles, once separated from their smaller companions, may be retained at a particular region while the smaller particles progress through the channel. Another feature would relate to the invention's ability to reconcentrate separated species that had become broadened and diluted. It is important recognize that the regions and their associated compartments may be of different sizes and, under some circumstances, might not be transverse to the direction of flow. FIG. 5 shows an example of different compartment and frit configurations.

Figure 6:
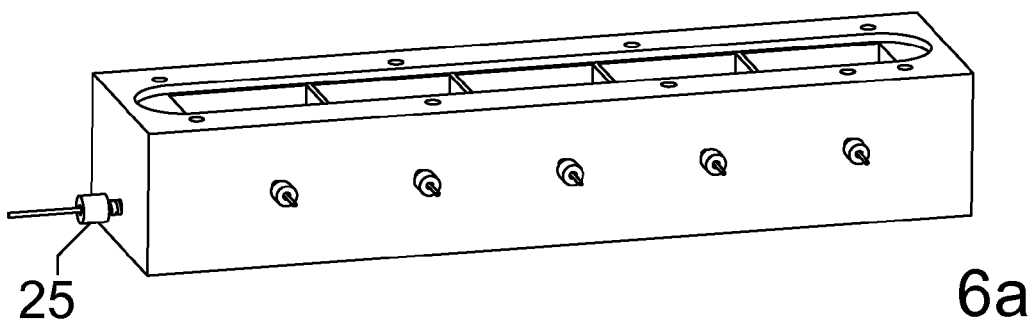
FIG. 6 shows front, rear and top views of the modified structure of FIG. 4 to allow its operation as the conventional A4F unit of FIG. 1.
Figure 6:
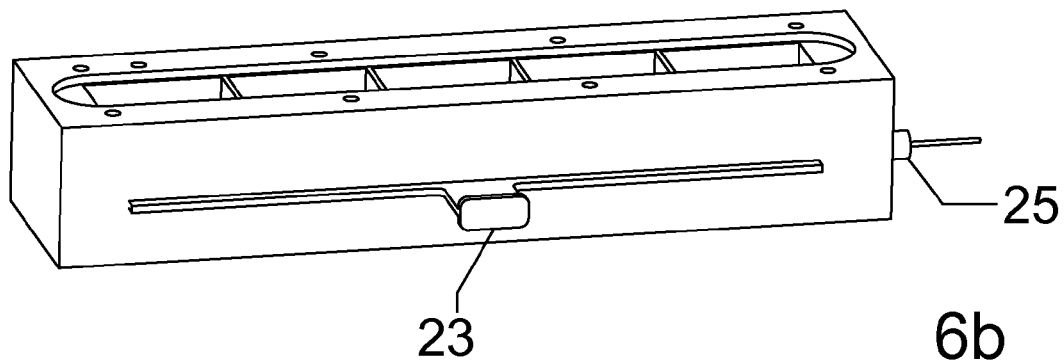
Figure 6:
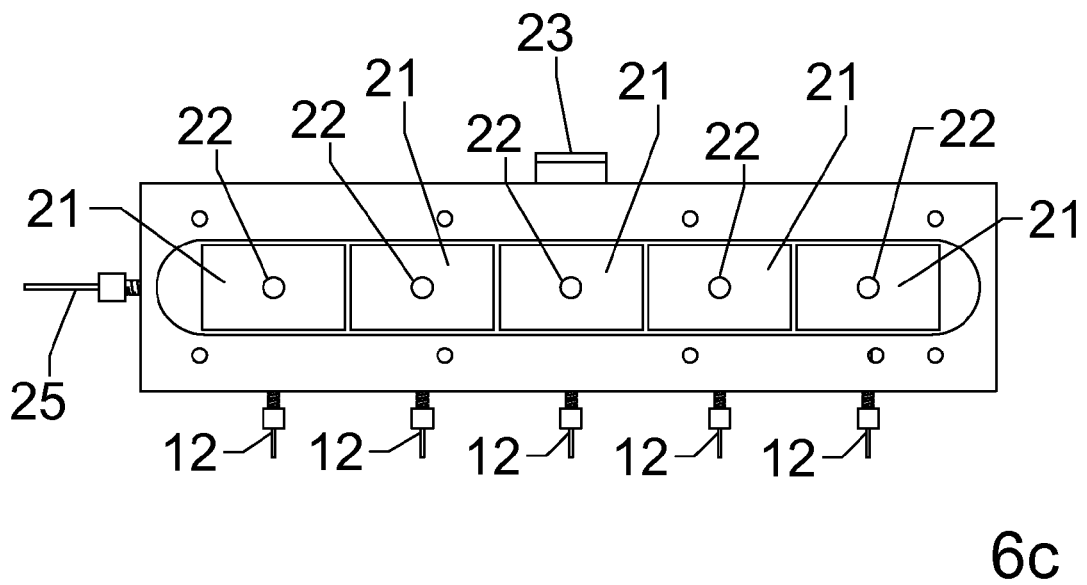
Figure 7:
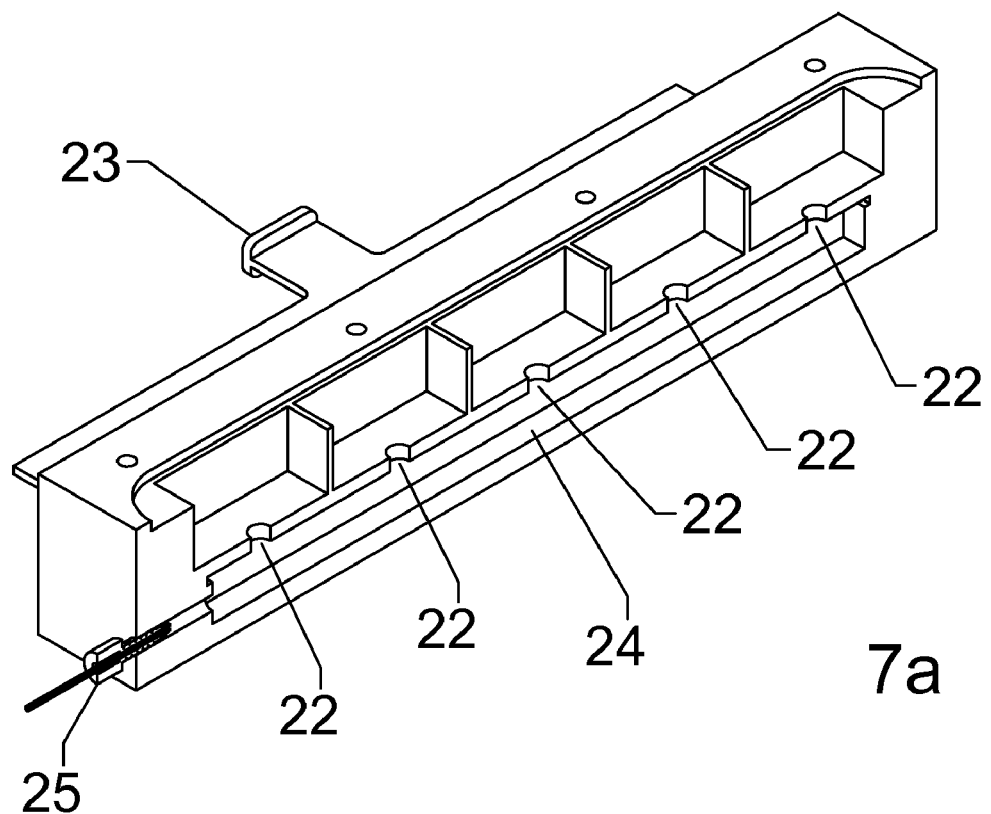
FIG. 7 shows isometric cutaway and side cutaway views of the structure of FIG. 6.
Figure 7:
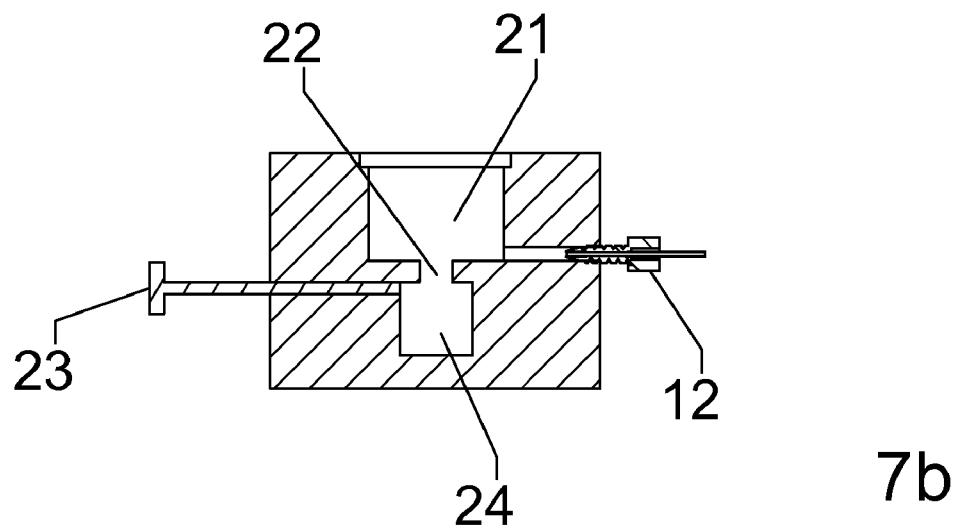

Referring again to FIG. 4 wherein the preferred embodiment is illustrated by a channel comprised of 5 equally sized regions, each with its corresponding compartment below, means by which the embodiment may be restored to its conventional form is readily visualized. FIGS. 6 and 7 suggest how the base of each compartment could be modified to incorporate a drain hole 22 at its base; each such drain emptying into a common compartment 24 below. By opening all such drains and closing each needle valve that controls out flow through the individual port fittings 12, the common single compartment is provided with a single port fitting 12 whose out flow is controlled by a single regulator in the controller unit. The channel would thus be restored for conventional operation. Providing mechanical means by which such drains could be opened simultaneously is illustrated schematically by the paddle structure 23 that may be slid out partially, opening thereby all drain holes 22 directing fluid to flow into the common compartment 24 and out through the associated out flow port fitting 12. This concept may be further expanded to permit compartmental ganging to be applied to selected sets of compartments whose cross flows per unit area may be required to be the same. For those compartments, their regulators would be closed and their drainage valves opened by individual paddle features similar to the multi drain hole paddle structure 23 allowing drainage into the common compartment 24 controlled by its single port fitting 12 shown at the left of the structure in a plane at right angles to the individual compartment out flow fittings.

The structure of FIG. 6 is shown in further detail by means of the cross sectional cut through the compartmentalized structure indicated in FIGS. 7a and 7b. The out flow port fittings 12 of each compartment are shown in FIG. 6a. Note that FIG. 6a is very similar to the base of the unit of FIG. 4 but with the addition of a single out flow port fitting 12 serving the common compartment 24. Although restoration to conventional operation may be achieved by displacing the paddle element 23 and stopping all individual flows through their port fittings 12, it would be far easier for most experimental requirements just to replace the compartmentalized structure with a conventional cross flow unit. The main and most important reason that one might want to be able to restore the channel by repositioning the drain hole blocking paddle 23, illustrated in FIGS. 6b and 6c would be to examine in greater detail the performance of a specific channel. That channel's physical structure, such as its dimensions and associated membrane variation, if any, may vary with usage. Since flows through specific compartments at varying rates may have affected certain local regions of the membrane, restoration of the device to its conventional operating mode would permit rapid examination of membrane changes that might have occurred while it was so operated.

Figure 4:
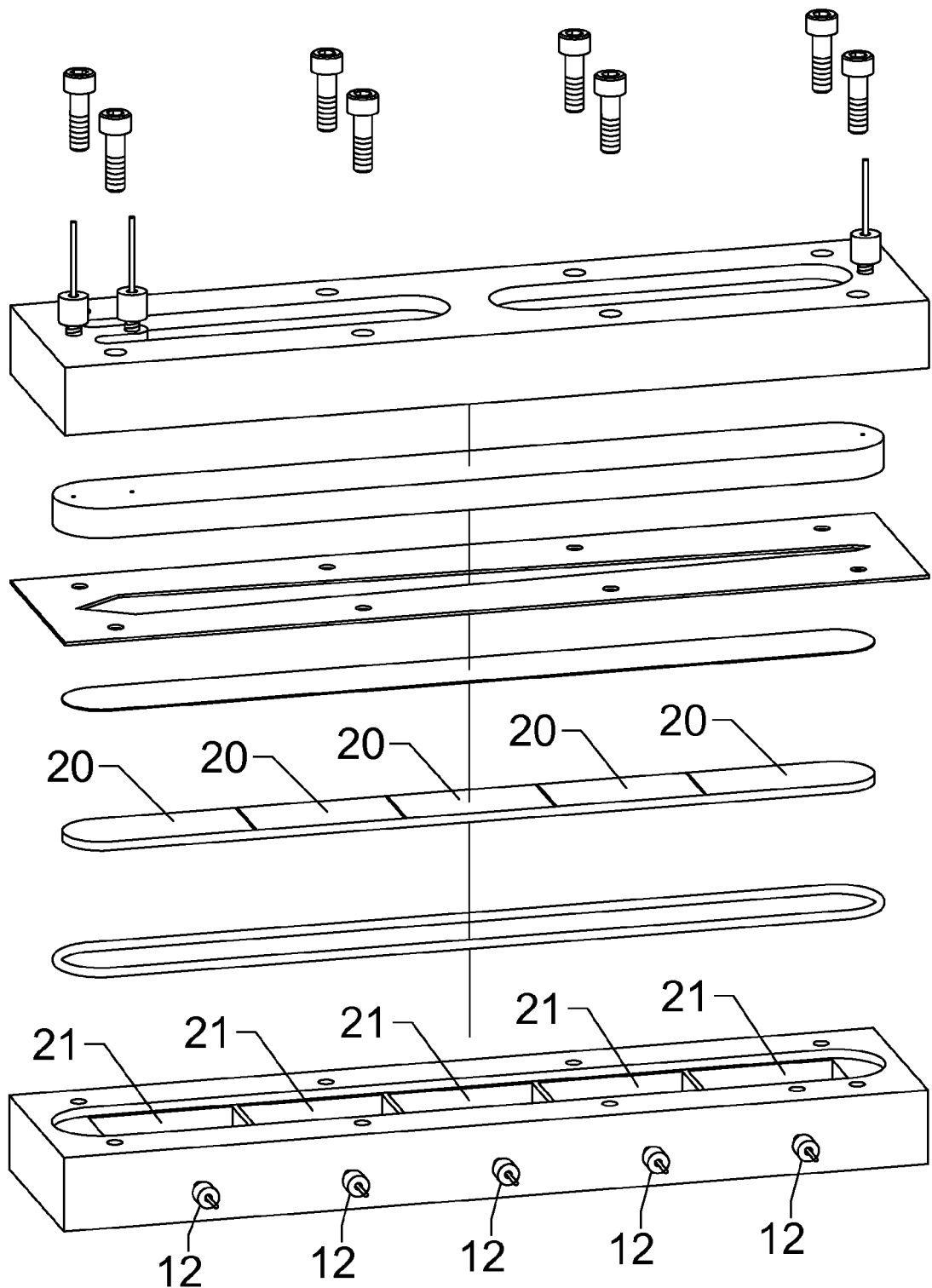
FIG. 4 shows the basic A4F structure modified to provide the inventive compartmentalized structure.
Figure 5:
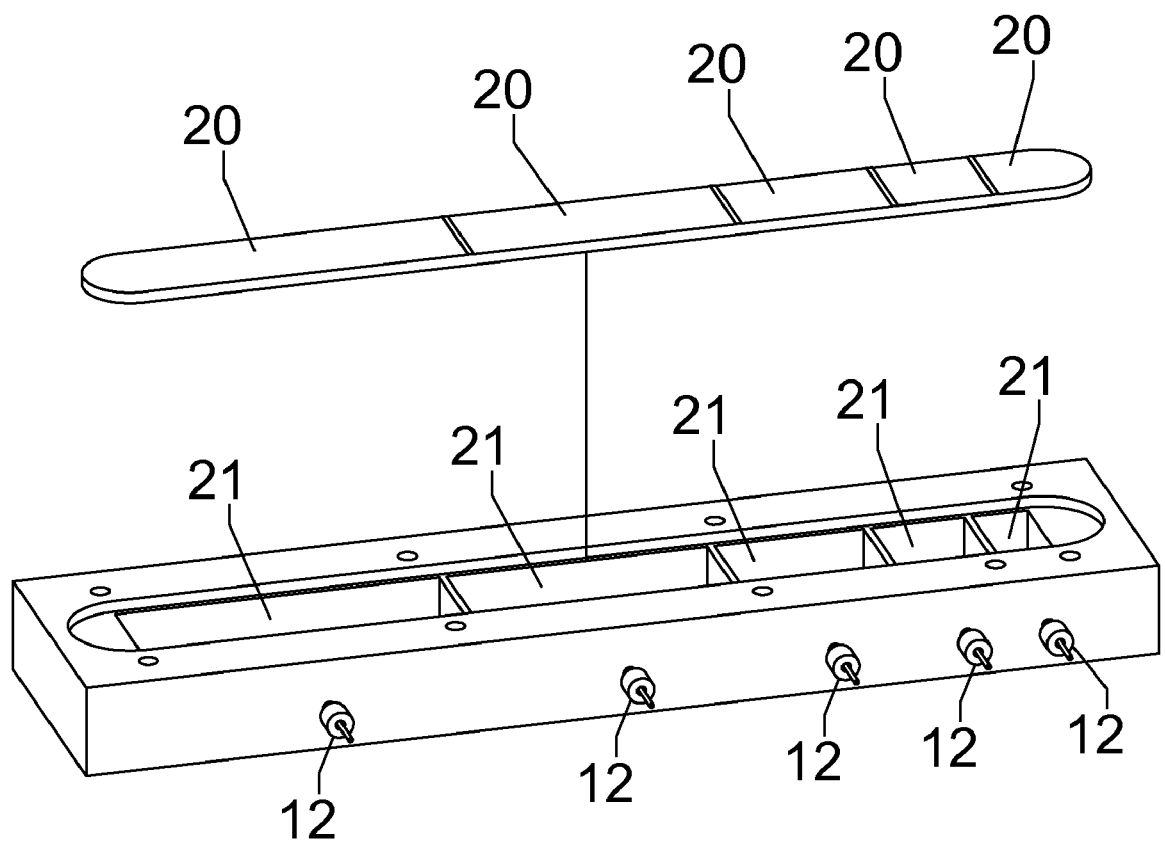
FIG. 5 illustrates the two key elements of FIG. 4 with different spacing between compartments.

Although FIG. 4 illustrates the invention by means of a five compartment configuration, it should be recognized, as discussed earlier, that similar systems may be developed using more or even fewer compartments of similar or different sizes. Means to gang different groups of compartments are easily implemented. Thus, in a 5-compartment device, there could be two sets of ganged compartments each with its regulating needle valve. For example, the first three and the fifth compartments might be controlled by a single regulating valve following the closure of their outflow port fittings 12 and the opening of their corresponding drainage holes into a single volume, while the fourth compartment could be controlled by a single valve controlling its outflow.

Figure 8:
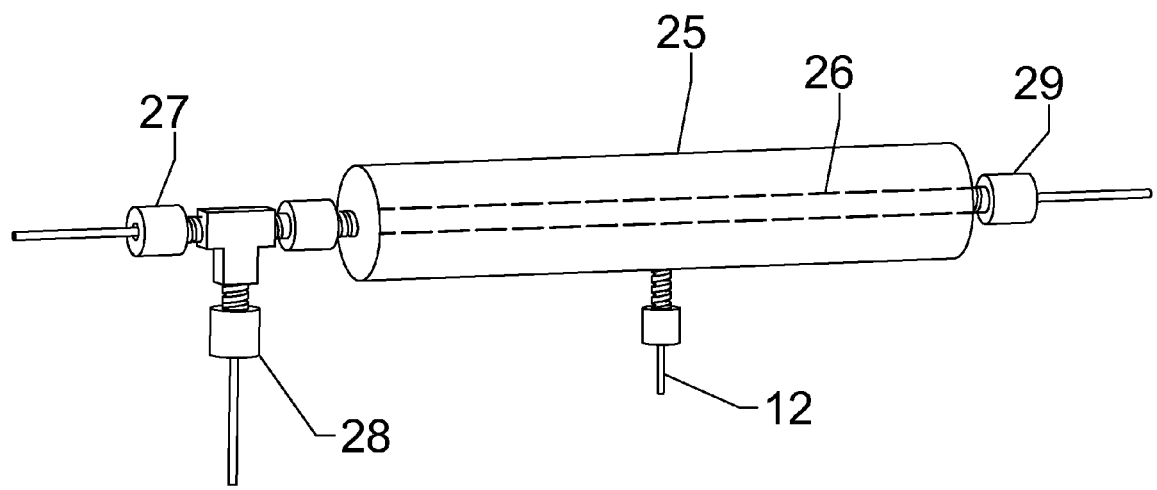
FIG. 8 shows the structure and key elements of a standard hollow fiber field flow fractionator, H4F, channel.

In order to illustrate further the universal application of the compartmentalization concept, reference is made to the hollow fiber FFF, H4F, device. FIG. 8 illustrates the structure and key elements of the porous hollow fiber fractionator. A rigid vessel 25 surrounds a porous cylindrical fiber 26 mounted therein between an inlet fitting 27 and exit port fitting 29. The mobile phase is introduced through fitting 27 and samples are injected into the mobile phase through injection port fitting 28. As the fiber is porous, its exudate flows into the vessel 25 and then out by means of regulation of such flow through exit port fitting 29 which is connected to the controller unit. The flow through the porous fiber channel 26 is comprised of two parts: transverse flow through the porous fiber and the longitudinal flow. Thus the fiber plays the role of the membrane/frit structure of the A4F and SF1FFF fractionators.

Figure 9:
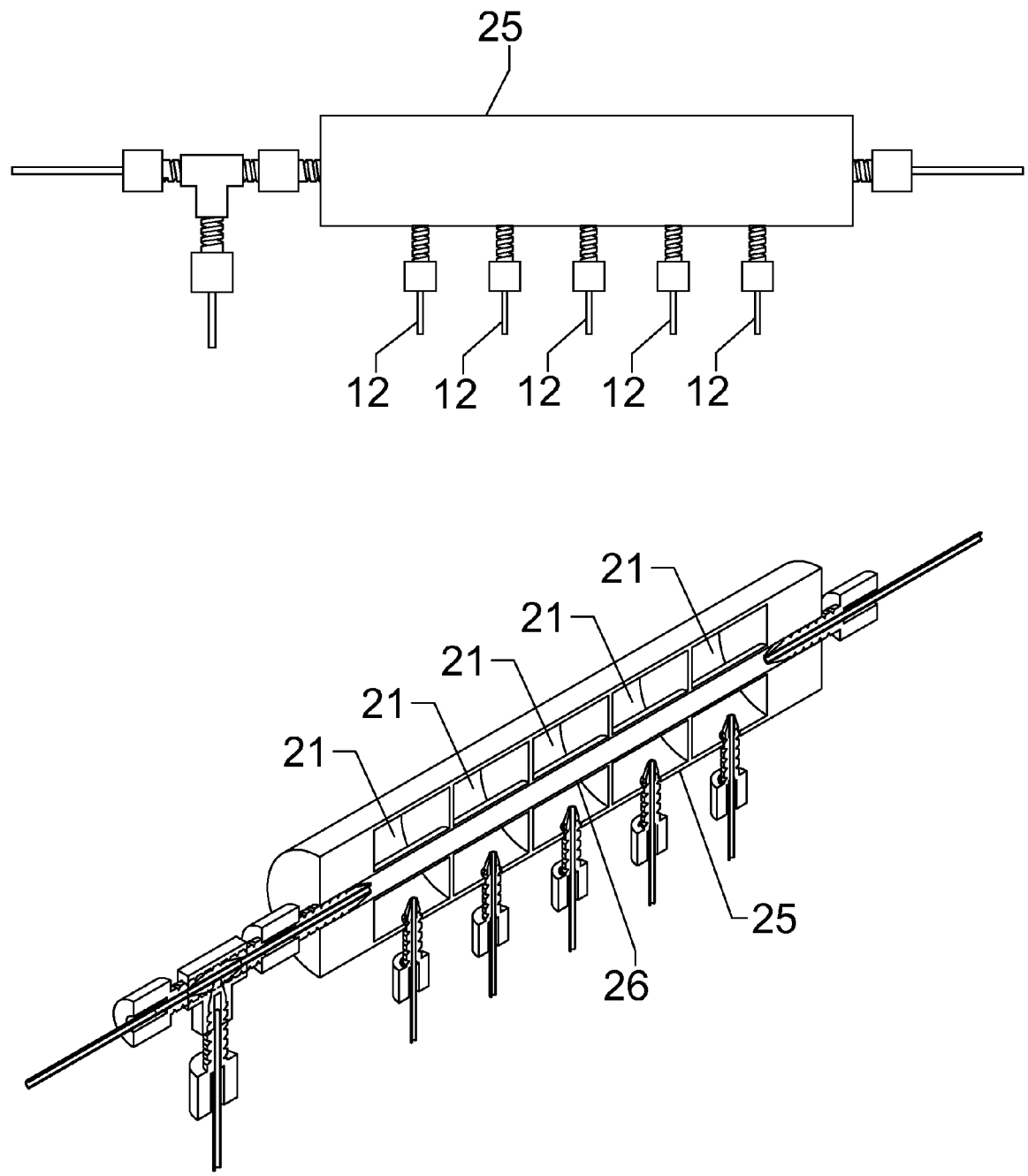
FIG. 9 shows a possible compartmentalized structure for a hollow fiber fractionator.

FIG. 9 illustrates how a porous hollow fiber fractionator, H4F, might be modified to permit compartmentalization similar to the A4F implementation. The internal structure of the modified rigid vessel 25 is divided into compartments 21 surrounding a porous fiber 26 threaded therethrough. The fiber may be cooled to shrink slightly before insertion producing a tight fit against the side walls of each compartment upon heating. Additionally, the internal pressure caused by the longitudinally flowing fluid therein may be sufficient to seal each compartment. For other types of porous hollow fibers that cannot seal by deformation means, circular O-rings may be inserted into each. Other implementations would include a compartmentalized vessel that is hinged into two axial components that are easily opened and provided with suitable seals and O-rings required for adequate sealing of each compartment.

Figure 10:
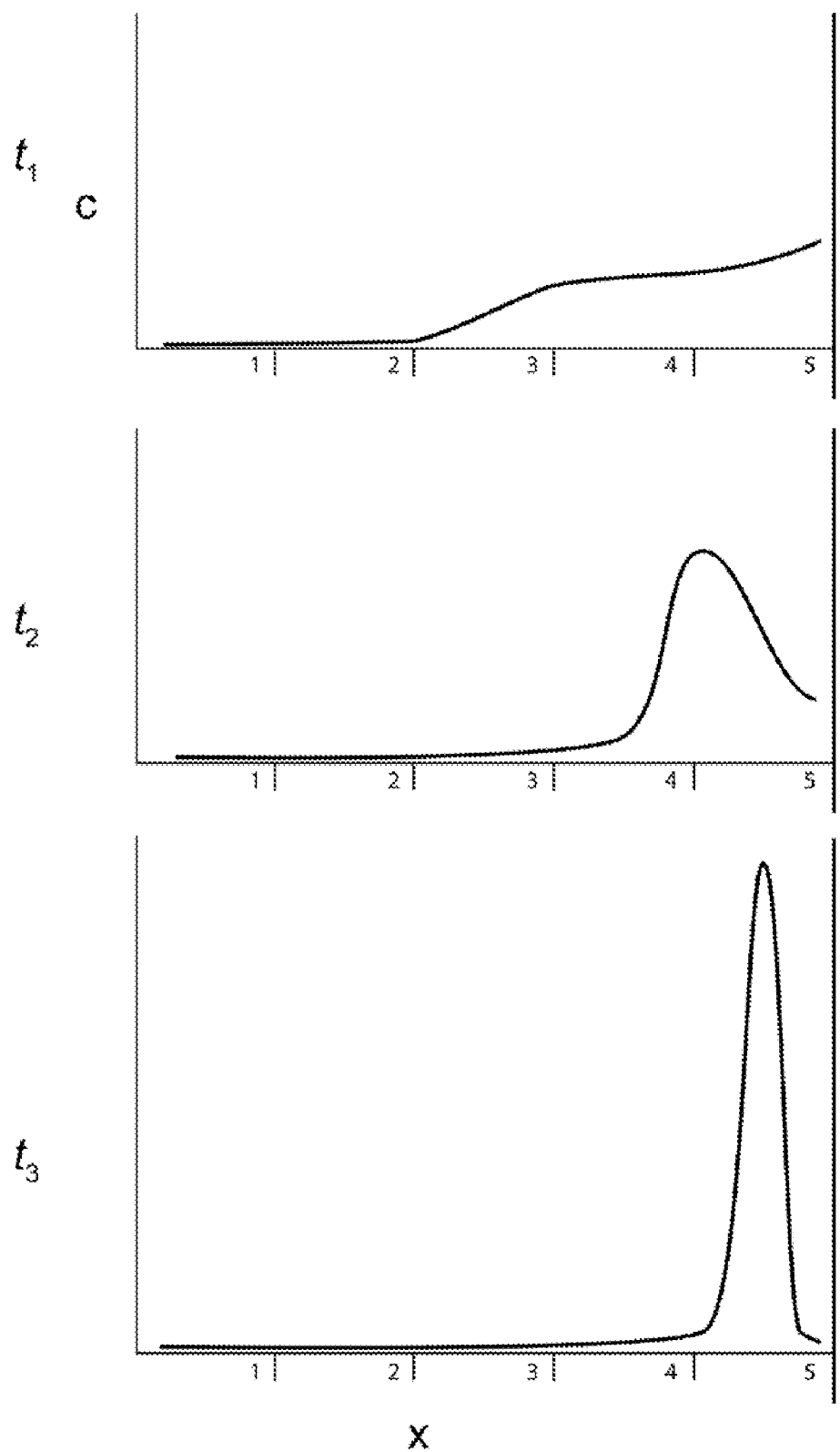
FIG. 10 is an example of an anticipated reconcentration of the aggregate rich fraction of the sample of FIG. 2 arising from a specific programmed set of cross flows.

FIG. 10 illustrates how the inventive technique might be used to examine the larger aggregates 19 of the sample shown in FIG. 2. Assume that an objective of this separation is to isolate and concentrate these larger aggregates 19 present from the most prominent oligomeric states. Assume also, that only 5 compartments are present. At $t=t_1$, most of the oligomeric peaks of the FIG. 2 sample have eluted and left the fractionator. The figure at this time shows the concentration of the remaining species as a function of channel position. Note that the five compartment positions are indicated by the numbers at the bottom of the graph. When most of the sample has fractionated and left the channel, the cross flow in the last compartment is increased significantly, retaining thereby much of the fraction 19 at the last two compartments. Other cross flows are maintained as they were throughout the separation, but the inlet mobile phase flow has been increased to accommodate the additional flows through the last two compartments. By $t=t_2$, the remaining sample is beginning to slow down and collect between these latter two compartments and by $t=t_3$, the cross flow through the fourth compartment has been stopped with the remaining sample being held at the last region shortly before it is released. In this manner, the unresolved aggregate fraction 19 has been further separated from the well defined and characterized oligomeric constituents. Once released, the aggregate fraction may be subjected to further analyses and study.

Although the membrane used for separations within a compartmentalized fractionator has been assumed of uniform composition, as have the individual frit elements, these constituents may be constructed with materials of different composition. For example, the membrane 4 of the A4F fractionators and, its compartmentalized variants, may be constructed of segmented sections fused or otherwise connected between regions. One segment, for example could be non porous preventing thereby any cross flow affecting the sample passing therethrough. Other membrane sections may be composed of sections with differing porosities. The supporting frits, as well, may be of differing compositions expanding or restricting thereby the flow therethrough. Consider a frit section composed of a highly porous material permeable to a broad range of molecular/particle sizes that might pass therethrough unimpeded. With a corresponding membrane section that is highly porous, any sample passing thereover at a particular time may be driven almost entirely therethrough by applying a strong cross flow as it reaches that porous section. Other cross flows at different compartments may be modified accordingly to establish means by which specific fractions of the separating sample may be collected and removed from therefrom.

Another interesting application of a simple compartmentalized fractionator would be one designed to collect specifically defined fractions of a sample undergoing separation. Consider that only the final compartment be operated independently in this manner with its corresponding membrane section almost completely permeable to any sample fraction that might pass therethrough. For most of the separation, cross flow would be prevented from passing through this section. Only when a specific fraction had reached it, would the cross flow be activated briefly and the fraction swept into its companion chamber. Since such a fractionator chamber may be of extremely small volume, other easily developed means may be required to extract such collected samples without their appreciable dilution.

The foregoing description, for purposes of explanation, used specific implementations to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible based on the above teachings. The particular embodiments described were chosen in order to best explain the principles of the invention and some of its many practical applications in order to enable, thereby, others skilled in the art to best utilize the invention and various embodiments with various modifications as are suited to the particular use contemplated. It is intended that the following claims and their equivalents define the scope of the invention.

The invention claimed is:

1. A flow field flow fractionator comprising a channel containment means, a base plate element, a permeable segmented frit, a permeable membrane, a top plate element and a sealing means, where
   A. said base plate element contains a plurality of distinct compartments open from above and fabricated to lie within said base, each of said distinct compartments having
      a. an opening lying in the same plane parallel to the base of said base plate;
      b. an exit port within each compartment permitting outflow therefrom of fluid that had entered it through said permeable membrane and corresponding fit segment lying thereover;
      c. fluid connection means from each such exit port to an independent fluid flow controlling means by which said outflow from each corresponding compartment may be controlled, permitting thereby the independent control of corresponding transverse flow on a sample aliquot as it moves over said corresponding compartment; in this manner, providing independently cross flow fields at each segmented region of said channel containment means;

B. elements of said permeable segmented frit lie on top of said compartment openings in said base plate with each said frit element covering a corresponding compartment thereunder;

C. said permeable membrane covers said segmented frit elements;

D. a spacer means on top of said permeable membrane from which has been cut out a section providing thereby said channel containment means, bounded on all sides by the remaining region of said spacer, said channel containment means spanning the segmented frit elements lying below said permeable membrane;

E. said top plate element lies on top of said spacer means sealing said channel containment means therefrom and providing three ports suitably positioned over said channel cutout; to permit, sequentially
  i. flow through of a mobile phase,
  ii. injection of said sample aliquot,
  iii. flow out of said sample that has been driven through said channel containment means by said mobile phase flow;

F. said sealing means restricts fluid introduced into said channel containment means to flow therethrough or transverse to said channel containment means through said permeable membrane and said supporting frit elements into compartments thereunder.

2. A symmetric implementation of the flow field flow fractionator of claim 1 where said top plate element is comprised of a permeable frit through which is pumped a secondary flow comprised of mobile phase perpendicular to flow along said channel containment means, said secondary flow providing source of all cross flow requirements of said segmented regions.

3. An asymmetric flow implementation of the flow field flow fractionator of claim 1 where said top plate element is impermeable to flow therethrough and total cross flow sources required for all controlled segmented regions is provided by restricting the channel outflow so that the difference between the channel inflow and this channel outflow is equal to the total cross flow of all segmented regions.

4. The flow field flow fractionator of claim 1 where said permeable membrane is segmented into regions of different permeabilities.

* * * * *